United States Patent [19]

Beineke

[11] Plant 4,954

[45] Nov. 23, 1982

[54] DISTINCT VARIETY OF BLACK WALNUT TREE

[75] Inventor: Walter F. Beineke, West Lafayette, Ind.

[73] Assignee: Purdue Research Foundation, West Lafayette, Ind.

[21] Appl. No.: 254,625

[22] Filed: Apr. 16, 1981

[51] Int. Cl.[3] ..... A01H 5/03

[52] U.S. Cl. ..... Plt./32

[58] Field of Search ..... Plt./32

*Primary Examiner*—Robert E. Bagwill

*Attorney, Agent, or Firm*—John R. Nesbitt

[57] ABSTRACT

A new and distinct cultivar of black walnut tree (*Juglans nigra L.*) which is distinctly characterized by extremely rapid growth rate, fairly strong central stem tendency, earlier than average time of leafing, and good straightness (little sweep and few crooks) thereby producing excellent timber qualities. The new variety has poor nut bearing qualities. Nut crops have been irregular and very light to none. This new variety of black walnut tree was discovered by the applicant in West Lafayette, Ind. in a yard area, and was discovered in the course of a search for unique and high quality black walnut trees to be utilized in breeding for outstanding timber producing potential. This selection has been designated as BW130 in records maintained on the performance of grafts made from the original selection and will be known henceforth as Tippecanoe-1.

3 Drawing Figures

BACKGROUND OF THE INVENTION

Figure 1:
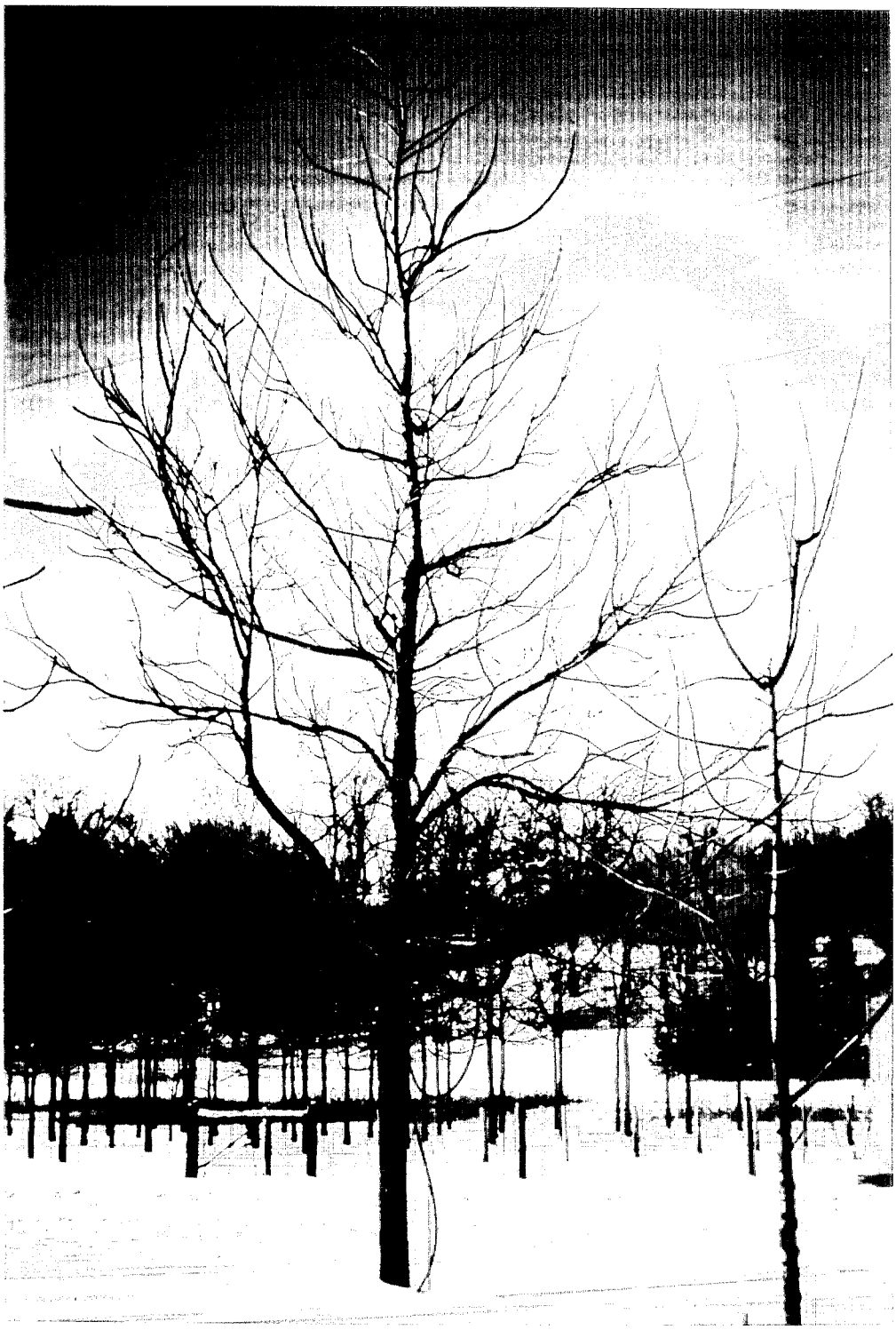
FIG. 1 is a photograph showing the timber form of Tippecanoe-1.
Figure 2:
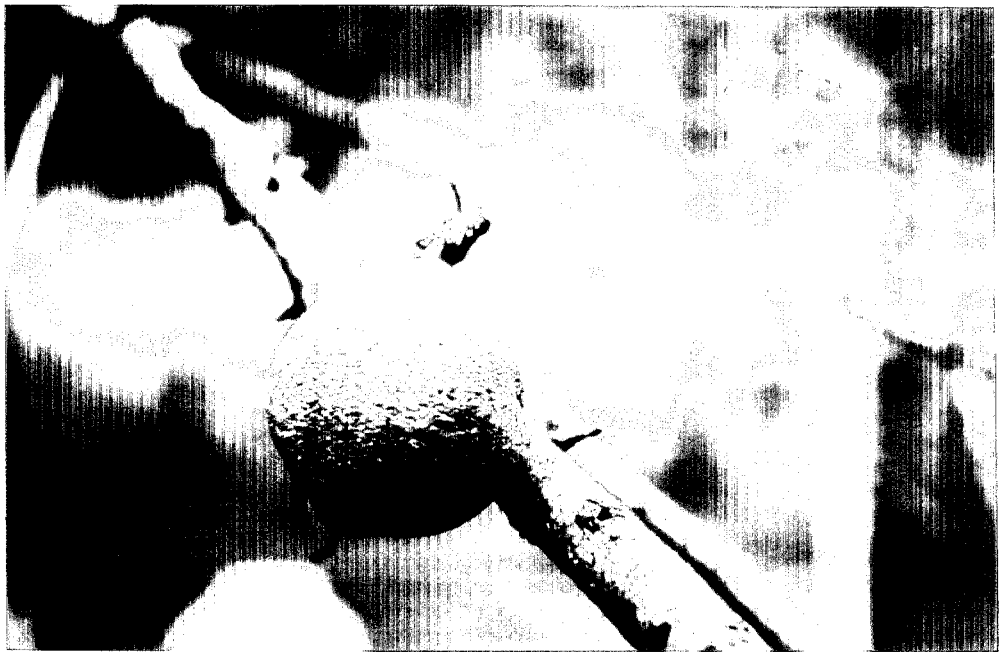
FIG. 2 is a photograph showing a twig with nuts attached from Tippecanoe-1.
Figure 3:
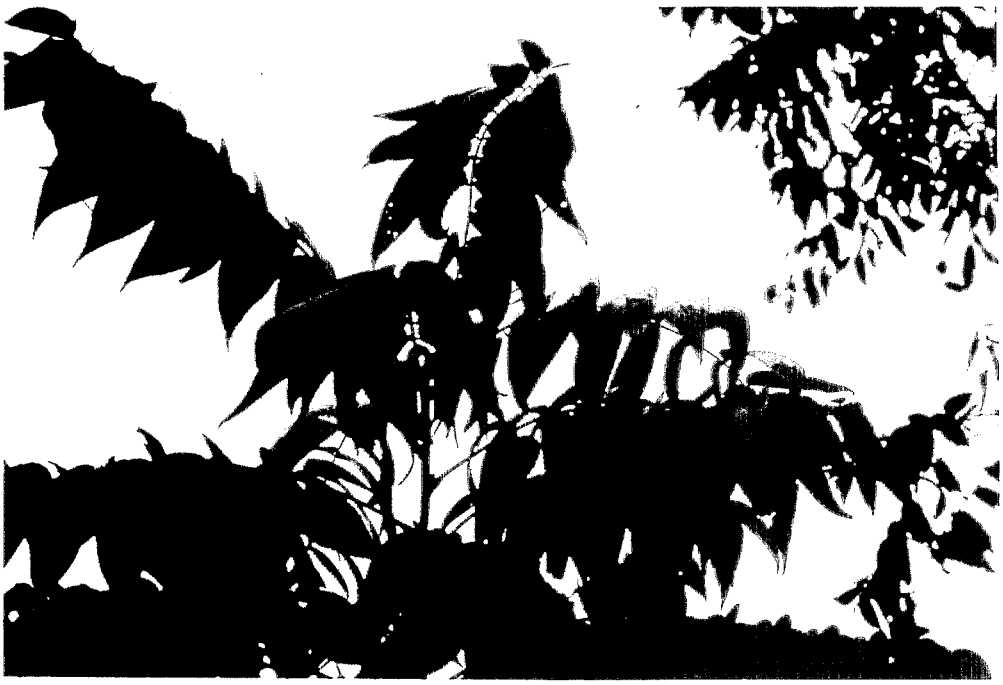

After the original clone was selected, and assigned an identity number of BW130, the aforesaid tree was reproduced by collecting scions from it and grafting these onto common black walnut rootstocks at Martell Forest, Purdue University. These asexual reproductions ran true to the parent tree and to each other in all respects.

The botanical details of this new and distinct variety of walnut tree are as follows:

Tree:

*Size.*—Large.

*Vigor.*—Vigorous.

*Growth rate.*—Very rapid, somewhat faster than Purdue 1 — 24% larger in diameter than the average of selected clones planted the same year, 13% taller than the average, and 53% more cubic foot volume than the average.

*Form.*—Good timber form, but somewhat poorer than Purdue 1 — 30% straighter than average on a rating scale of 1 to 5. Few crooks. Fairly strong central stem tendency.

Trunk:

*Bark.*—Dark brown to gray.

*Texture.*—Interlacing ridges.

Branches:

*Diameter.*—Large.

*Length.*—Long.

*Branch angle.*—Lower branches — 55 degree average.

*Foliage.*—Quantity — Abundant. Density — Heavy.

Leaves:

*Compound leaves.*—Size — about average; average length — 16½";

*Leaflets.*—Size — average; average length 4"; average width — 1½"; average number of leaflets — 20; shape — lanceolate; acutely pointed; Thickness — thin; Texture — smooth; Margin — serrated; Petiole — short; Color — Topside — dark green; Underside — light green.

*Anthracnose resistance.*—Poorer than average on a rating scale of 1 to 5.

*Time of leafing.*—Early — averages 4 days earlier or 37% earlier than average.

Flowering habit:

*Age at which tree starts producing catkins.*—Very late.

*Number of catkins produced.*—Few.

*Size of catkins.*—Large.

*Time of pollen shed.*—Late.

*Age at which time tree starts producing pistillate flowers.*—Very late.

*Number of pistillate flowers produced by young trees*—.—Few.

*Number of pistillate flowers produced by mature trees.*—Few.

*Lateral shoots producing pistillate flowers.*—None.

*Number of pistillate flowers per inflorescence.*—2.

*Timing of pistillate flower receptivity.*—Very late.

*Coincidence of staminate and pistillate bloom.*—Fair.

Nut crop:

*Bearing.*—Irregular.

*Productivity.*—Very light to none.

*Ripening period.*—Early.

*Evenness of maturity (period between first and last nuts are ready for harvest).*—Unknown.

*Quality.*—Fair.

*Distribution of nuts on tree.*—Unknown.

Hull:

*Outer surface.*—Smooth.

*Form.*—Pointed blossom end.

*Thickness.*—Medium.

*Size.*—Medium; average length — 2 5/16"; average diameter in suture plane — 1⅞"; average diameter cheek to cheek — 2⅛".

Nut:

*Size.*—Medium to large; average length — $1\frac{3}{8}''$; average diameter in suture plane — 1 7/32"; average diameter cheek to cheek — $1\frac{1}{2}''$.

*Uniformity of size.*—Some variation.

*Form.*—Flattened in suture plane and round.

*Blossom end.*—Rounded.

*Basal end.*—Rounded.

*Weight.*—Dry weight of ten nuts — 170.8 gm; dry weight of ten kernels — 26.5 gm; average percentage kernels to nut — 15.5%.

*Thickness of shell.*—Thick.

*Fill.*—Fair.

Kernel:

*Size.*—Large.

*Plumpness.*—Plump.

*Shrivel.*—None.

*Flavor.*—Good.

*Color.*—Light.

The walnut tree and its nuts herein described may vary in slight detail due to climatic and soil conditions under which the variety may be grown; the present description being of the variety as grown near West Lafayette, Ind.

I claim:

1. A new and distinct variety of black walnut tree substantially as illustrated and described, which has excellent timber quality, is fast growing, has fairly strong central stem tendency, little sweep, few crooks; earlier than average in time of leafing, and low nut production.

* * * * *